US010765339B2

(12) United States Patent
Gärber

(10) Patent No.: US 10,765,339 B2
(45) Date of Patent: Sep. 8, 2020

(54) DEVICE AND METHOD FOR DETERMINING A CIRCUMFERENTIAL SHAPE OF AN ELECTRODE ARRAY FOR ELECTRICAL IMPEDANCE TOMOGRAPHY

(71) Applicant: Drägerwerk AG & Co. KGaA, Lübeck (DE)

(72) Inventor: Yvo Gärber, Breitenfelde (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 311 days.

(21) Appl. No.: 15/825,955

(22) Filed: Nov. 29, 2017

(65) Prior Publication Data

US 2018/0146882 A1 May 31, 2018

(30) Foreign Application Priority Data

Nov. 30, 2016 (DE) .................. 10 2016 014 252

(51) Int. Cl.
| | |
|---|---|
| *A61B 5/05* | (2006.01) |
| *A61B 5/053* | (2006.01) |
| *A61B 5/00* | (2006.01) |

(52) U.S. Cl.
CPC .......... *A61B 5/0536* (2013.01); *A61B 5/6823* (2013.01); *A61B 5/6844* (2013.01); *A61B 5/7225* (2013.01); *A61B 5/7221* (2013.01); *A61B 2560/0475* (2013.01); *A61B 2562/043* (2013.01)

(58) Field of Classification Search
CPC ... A61B 5/0536; A61B 5/6823; A61B 5/6844; A61B 5/7225; A61B 5/7221; A61B 2560/0475; A61B 2562/043
See application file for complete search history.

(56) References Cited

U.S. PATENT DOCUMENTS

| | | | |
|---|---|---|---|
| 5,184,624 | A | 2/1993 | Brown et al. |
| 5,807,251 | A | 9/1998 | Wang et al. |
| 6,236,886 | B1 | 5/2001 | Cherepenin et al. |
| 2013/0096425 | A1 | 4/2013 | Uutela et al. |
| 2016/0302690 | A1 | 10/2016 | Nebuya et al. |

FOREIGN PATENT DOCUMENTS

| | | |
|---|---|---|
| WO | 2015/025113 A1 | 2/2015 |
| WO | 2015/048917 A1 | 4/2015 |

*Primary Examiner* — Bo Joseph Peng
(74) *Attorney, Agent, or Firm* — McGlew and Tuttle, P.C.

(57) ABSTRACT

An electrical impedance tomography device (1) includes an electrode array, including a plurality of electrodes (33) arranged spaced apart from one another, a signal feed unit (51) and a signal acquisition unit (50). A calculation and control unit (70) is configured to determine a current elliptical circumferential shape (20') of the electrode array on a thorax (34) of a human being and to provide a control signal (79), which indicates the elliptical circumferential shape (20) of the electrode array. The calculation and control unit (70) may be configured as a central unit or an array of distributed units (cloud computing) in order to determine and to provide the current elliptical circumferential shape (20').

8 Claims, 5 Drawing Sheets

DEVICE AND METHOD FOR DETERMINING A CIRCUMFERENTIAL SHAPE OF AN ELECTRODE ARRAY FOR ELECTRICAL IMPEDANCE TOMOGRAPHY

CROSS REFERENCE TO RELATED APPLICATIONS

This application claims the benefit of priority under 35 U.S.C. § 119 of German Application 10 2016 014 252.9, filed Nov. 30, 2016, the entire contents of which are incorporated herein by reference.

FIELD OF THE INVENTION

The present invention pertains to an electrical impedance tomography device with determination of a circumferential shape of an electrode array associated with the electrical impedance tomography device.

The present invention further pertains to a method for the operation of an electrical impedance tomography device with determination of a circumferential shape of an electrode array associated with the electrical impedance tomography device.

BACKGROUND OF THE INVENTION

Electrical impedance tomography (EIT) devices are known from the state of the art. These devices are configured and intended to generate signals obtained by electrical impedance measurements and data and data streams obtained therefrom, an image, a plurality of images or a continuous series of images. These images or series of images show differences in the conductivity of various body tissues, bones, skin, body fluids and organs, especially of the lung, which are useful for observation of the patient situation.

Thus, U.S. Pat. No. 6,236,886 describes an electrical impedance tomograph comprising an array of a plurality of electrodes, current feed to at least two electrodes, signal acquisition at the other electrodes and a method with an algorithm for image reconstruction to determine the distribution of conductivities of a body, such as bones, skin and blood vessels in a basic configuration comprising components for signal acquisition (electrodes), signal processing (amplifier, A/D converter), current feed (generator, voltage-current converter, current limitation) and control components.

It is stated in U.S. Pat. No. 5,807,251 that it is known to provide a set of electrodes, which are arranged at a defined distance from one another, for example, around the thorax of a patient in electrical contact with the skin, in the clinical application of EIT. Electrodes arranged adjacent to one another, each alternating between different electrodes or all of the possible pairs of electrodes, are applied for an electrical current or voltage input signal. While the input signal is applied to one of the pair of electrodes arranged adjacent to one another, the currents or voltages between each pair of remaining electrodes adjacent to one another are measured, and the measured data are processed in a known manner in order to obtain a visualization of the distribution of the specific electrical resistance over a cross section of the patient, around whom the ring of electrodes is arranged, and to display same on a display screen.

Unlike other imaging radiological methods (X-ray machines, radiological computer tomographs), electrical impedance tomography (EIT) has the advantage that radiation exposure, which is disadvantageous for the patient, does not occur. Unlike sonographic methods, a continuous acquisition of images over a representative cross section of the entire thorax and the lungs of the patient by means of the electrode belt can be carried out using EIT. In addition, the need to use a contact gel, which has to be applied before each examination, is omitted. Electrical impedance tomography (EIT) thus offers the advantage of making a continuous monitoring of the lungs possible in order to observe and to document a course of therapy of a mechanically ventilated or spontaneously breathing patient.

As is known, for example, from U.S. Pat. No. 5,807,251, an impedance measurement is carried out using an EIT device on the thorax by means of an electrode array around the thorax of a patient, and an image of the lungs of the patient is generated from the impedances by means of a conversion to the geometry of the thorax.

With a total number of, for example, 16 electrodes arranged around the thorax of a patient, an EIT device can generate a 32×32-pixel image of the lungs in a circulation of current feeds to each of two electrodes and a pickup of voltage-measured values (EIT measured signals) at the remaining electrodes. In this connection, at the 16 electrodes, a number of 208 impedance measured values is acquired at the electrodes. A quantity of 1,024 pixels is then obtained from these 208 impedance measured values using the EIT image reconstruction.

The electrodes are arranged in a horizontal array around the thorax of a living being and comprising an area of the lungs of the living being for carrying out the electrical impedance tomography (EIT). This results in a position in the plane of the electrode array, which can be designated as a thoracic-axial position of the electrode array on the circumference of the transverse plane of the body.

When an electrode belt is used as an electrode array, in or at which the electrodes are arranged and held at fixed positions with defined distance to one another, the chances of deviations in the vertical position between adjacent electrodes to one another on the thorax are comparatively small. Thus, a vertical shift during the image reconstruction, in which a horizontal tomogram through the thorax is determined as a so-called dorsal view, plays a comparatively minor role in the positioning of the electrode belt on the thorax. The horizontal tomogram is in this case imaged inclined only by a few degrees. In addition, electrical fields are obtained not only in the section plane itself, but also in areas above and below of approx. 5 cm to 10 cm of the section plane each, which are then also incorporated into the impedance measurements in any case, during the electrical feed to the electrodes. As a consequence, the only slightly possible inclination of the electrode belt in the tidal image is virtually imperceptible as an effect. Moreover, a comparatively reproducible and representative horizontal position of the electrode belt during application can be achieved due to an orientation at the costal arches, so that possible errors in the horizontal attachment of the electrode belt to the thorax occur rather rarely.

By contrast, the horizontal position of the electrodes is important because the physiologically expected, almost elliptical geometry of the thorax, which deviates from the ideally round, circular or cylindrical shape, is important for the generation of the dorsal view because information is necessary for an incorporation of the elliptical shape into the image reconstruction on which electrode is arranged on the thorax and in which position, i.e., front (sternum), lateral (costal arches) or rear (spine). Various types of living beings, in whom it is common for gas exchange to occur in them by means of lung breathing, have each circumferential shapes, which are typical in themselves, in the body structure surrounding the lungs (muscles, skeleton, organs, body tissues, skin). A deviation of the shape of the thorax from an ideal circular shape is, for example, given in human beings, in principle, to the effect that the typical circumferential shape is, as a rule, a rather elliptical than circular shape. In other living beings, such as horses, dogs, pigs, rodents or birds, other typical shapes of the circumferential shapes result depending on the species of animal. In this respect, an idea of the present invention, of using the electrical impedance tomography device to provide a determination of a circumferential shape of an electrode array positioned on the body and associated with the electrical impedance tomography device, can be extrapolated not only to the application of electrical impedance tomography in human beings, but also to a broad biodiversity of the animal kingdom. In human beings, especially the area of the electrode plane being used during the electrical impedance tomography (EIT), i.e., the plane in the horizontal section through the thorax, approximately in the area of the third, fourth, fifth costal arch, as well as of the fifth, sixth, seventh thoracic vertebra, has an elliptical circumferential shape (ellipsoid) in the area of the upper part of the body and of the thorax. In addition to the geometric shape with an anatomically predefined elliptical configuration area, there are additional characteristic features, which have an effect on the impedance, impedance differences and impedance distribution measured by means of EIT and have an effect during the image reconstruction on the visualization of the ventilation of the lungs in a transverse view, or are taken into consideration in the mathematically-algorithmically applied manner of the image reconstruction, just as the elliptical circumferential shape. Thus, in addition to the lung, with areas supplied with blood in the rhythm of the heartbeat and ventilated in the rhythm of the breathing cycle, the heart, with areas supplied with blood essentially in the rhythm of the heartbeat, but quasi permanently in a similar manner, elements of the skeleton, the sternum in the front-side area of the upper part of the body and the spine in the rear-side area, the impedances of which are both unaffected by blood supply and breathing cycle, are, in addition, arranged in this electrode plane. Both the sternum and especially the spine have instead an impedance that deviates from these areas and other areas (heart, skin lungs, tissue) in the electrode plane and is essentially constant.

An ellipse can be described as a closed oval shape, as a deviation from a circular shape, and as a dimensionless number by means of so-called eccentricity.

In this case, eccentricity describes the relationship of the two half-axes, which are at right angles to one another. Both half-axes are of identical length in case of a circle, and an ellipse is defined by a shorter half-axis and a longer half-axis, compared to the shorter half-axis, of different lengths. Due to the elliptical shape and depending on the eccentricity thereof, different distances arise between the feeding electrodes and the measuring electrodes located opposite them depending on whether the feed takes place on the front-side area with measurement on the rear-side area, or the feed takes place on the rear-side area with measurement on the front-side area along the frontal plane of the human body, or whether the feed takes place on the left side of the body with measurement on the right side of the body, or the feed takes place on the right side of the body with measurement on the left side of the body along the transverse axis of the human body. The two feed/measurement constellations located opposite one another on the left/right side of the body represent feeds/measurements on the longer half-axis in the elliptical circumferential shape of the human body and the two feed/measurement constellations located opposite one another on the front side of the body/on the rear side of the body represent feeds/measurements on the shorter half-axis in the elliptical circumferential shape of the human body.

The circumferential shape of the thorax at the location of the attachment of the electrodes is found directly in the circumferential shape of the electrode array positioned on the thorax and holding the electrodes again, since the electrode array is typically configured as a largely flexible and movable, and usually elastic electrode belt, so that the electrode array follows the circumferential shape at the location of the positioning. Deviation of the circumferential shape of the thorax or of the electrode array from a typical or average elliptical shape has an effect on the use of electrical impedance tomography (EIT), since the circumferential shape with the average elliptical shape is incorporated into the reconstruction algorithm for image reconstruction by means of the reconstruction algorithm. This means that the average elliptical circumferential shape of the thorax, which arises due to the different lengths of the two half-axes and, as was explained above, which can be defined by means of eccentricity as a predefined variable, is included in the reconstruction algorithm. In the real application, i.e., the attachment of the electrode array around the thorax, more or fewer deviations of the real circumferential shape from the average elliptical circumferential shape of the horizontal plane of the electrode array as well as above and below the electrode array on the respective patient occur depending on the respective patient. These deviations from the average elliptical circumferential shape in, as well as above and below the electrode array have an effect on the result of the image reconstruction, since the reconstruction algorithm determines and provides a pictorial visualization of the ventilation of the lung areas in a dorsal view of the thorax, in which deviations, for example, are present in the form of the surface visualization of the lungs and thorax, without an adaptation of the reconstruction algorithm to the deviations of the real circumferential shape from the average elliptical circumferential shape. A possibility of taking into account deviations from the average elliptical circumferential shape in the electrode plane may take place, for example, by the real lengths of the two half-axes of the ellipse and of the circumference of the thorax of the patient in the electrode plane being measured by the clinical staff and being made available to the electrical impedance tomography (EIT) device by means of a manual input. A real elliptical circumferential shape can then be determined in the electrical impedance tomography (EIT) device, which then makes it possible to adapt the reconstruction algorithm for determination of a pictorial visualization of the ventilation of lung areas, which has been corrected by the circumferential shape or by the deviation of the circumferential shape compared to the average elliptical circumferential shape. For application in routine clinical practice, both individual measurements of the thorax and the resulting manual inputs at the device with expenditure of time and with possibilities for errors (erroneous measurements, input errors) are linked to the clinical staff; both are disadvantageous and adverse in the daily routine clinical practice.

An electrical impedance tomography system is shown in WO 2015/048917 A1. The EIT system is suitable for acquiring electrical properties of a lung of a patient as impedances. For this, the impedance values and impedance changes of the lung are acquired by means of feeding voltage or current between two or more electrodes and a signal acquisition at an electrode array and then further processed by means of data processing. The data processing comprises a reconstruction algorithm with a data processor in order to determine and to reconstruct the electrical properties from the impedances. In case of the reconstruction of the electrical properties from the acquired measured data, an anatomical model is adapted from a plurality of anatomical models on the basis of the biometric data of the patient selected and the reconstruction of the EIT image data on the basis of the anatomical model and of the biometric data. This adaptation requires that biometric data be inputted into the system by the user. In this connection, age, gender, height as well as a circumference of the thorax of the patient are to be inputted under biometric data. This means that boundary conditions are to be inputted by the user before the beginning of the measurement with the electrical impedance tomography system in order to be able to select and apply a suitable reconstruction model, which is based on a selected anatomical model.

For the operation of electrical impedance tomography systems, it is not really advantageous in many application situations to have to measure or acquire and input a plurality of patient data before the beginning of the application. In particular, the need for data that refer to the properties of the body such as circumference of the thorax, height and weight assumes that the anatomical models stored in the device can also be used for a plurality of patients.

SUMMARY OF THE INVENTION

Knowing the above-described drawbacks of the known prior art, an object of the present invention is to provide an electrical impedance tomography (EIT) device suitable for an imaging of the lungs with an electrode array, which is associated with the electrical impedance tomography device and which makes possible a determination of a deviation of a circumferential shape of an electrode array positioned on a body of a patient from an average circumferential shape.

Furthermore, an object of the present invention is to provide an electrical impedance tomography (EIT) device suitable for an imaging of the lung with an electrode array, which is associated with the electrical impedance tomography device and which may take into consideration the deviation from the average circumferential shape when determining and imaging a tidal image of the lung.

Another object of the present invention is to provide a method for the operation of an electrical impedance tomography (EIT) device suitable for an imaging of the lung, which makes it possible to determine a deviation of a circumferential shape of an electrode array positioned on the body from an average circumferential shape.

The method may be provided or implemented as a computer program or computer program product, so that the scope of protection of the present application likewise extends to the computer program product and the computer program.

Initially, some of the terminology used within the scope of this patent application shall be explained in detail.

Observation period is defined as a time period in a time course in the sense of the present invention. The beginning and end of such an observation period are given either by fixed or adjustable times or by events, which are given due to the breathing or ventilation properties. Examples of observation periods, which are oriented towards breathing or ventilation, are a breathing cycle, a plurality of breathing cycles, segments of breathing cycles, such as inhalation (inspiration), inspiratory pause, exhalation (expiration), expiratory pause.

EIT measured signals are defined in the sense of the present invention as subsequent signals or data that can be acquired with an EIT device by means of a set of electrodes or by means of an electrode belt. For this, EIT measured signals are included in different signal characteristics, such as electric voltages or voltage measured signals, electric currents or current measured signals, associated with electrodes or sets of electrodes or with positions of electrodes or sets of electrodes on the electrode belt, as well as electric resistance or impedance values derived from voltages and currents.

Measuring run is defined in the sense of the present invention as a signal feed to two feeding electrodes, a so-called pair of feeding electrodes, during which acquisitions of EIT measured signals are made at other electrodes different from these two feeding electrodes.

Measuring cycle is defined in the sense of the present invention as a sequence of feeds to a plurality of pairs of feeding electrodes each with a corresponding measuring run at the remaining electrodes. Such a measuring cycle is in this case typically designated as a so-called "frame" or "time frame" in case of a processing of EIT data.

An EIT system with a number of 16 electrodes with use of an adjacent data acquisition mode results in a number of 208 measured signals in a measuring cycle, i.e., in a "time frame."

A measuring run as a part of a measuring cycle is correspondingly typically designated as a "partial frame" in case of the processing of EIT data. A number of 13 measured signals is obtained in a measuring run, i.e., in a "partial frame" in case of an EIT system having a number of 16 electrodes with use of an adjacent data acquisition mode.

The use of the adjacent data acquisition mode means that the 13 measured signals in a measuring run are acquired from two electrodes positioned adjacent to one another as pairs of measuring electrodes based on a feed to the two electrodes positioned adjacent to one another as a pair of feeding electrodes. From each of the pairs of two electrodes positioned adjacent to one another, as pairs of measuring electrodes, 16 measured signals are obtained in a measuring cycle with rotation of the pair of feeding electrodes with the 16 measuring cycles for each pair of measuring electrodes.

An EIT measuring channel is defined in the sense of the present invention as an unambiguous association or constellation of two signal-feeding electrodes and two signal-acquiring electrodes each, which are different from the two signal-feeding electrodes, from a plurality of electrodes. The plurality of electrodes are configured as a component of the electrical impedance tomography device by means of an electrode array, which is configured, for example, as an electrode belt with a defined number of electrodes arranged around the thorax of a patient. Exemplary numbers of electrodes in the electrode belt are 16, 32 or 64 electrodes. There are a plurality of EIT measuring channels, which comprise different associations or constellations of feeding electrodes, on the one hand, and measuring electrodes different therefrom, on the other hand. The EIT measuring channels are preferably addressed in the form of an index-based manner and the data acquired on the EIT measuring channels are preferably addressed in the form of indexed vectors, indexed data fields or indexed matrices, stored and kept ready for further processing (vector operations, matrix operations). In case of an EIT system with a number of 16 electrodes with use of an adjacent data acquisition mode, there are 208 EIT measuring channels, wherein one measuring channel each is defined as a clear association of a pair of feeding electrodes and a pair of measuring electrodes. In the adjacent data acquisition mode, two adjacent electrodes of the plurality of electrodes are each used for feeding and two adjacent electrodes of the remaining electrodes from the plurality of electrodes are used for signal acquisition.

A device according to the present invention is provided according to a first aspect of the present invention.

The electrical impedance tomography device according to the present invention is for a determination of an elliptical circumferential shape of an electrode array associated with the electrical impedance tomography device and positioned on a body of a patient. The electrical impedance tomography device according to the present invention comprises: an electrode array; a signal feed unit; a signal acquisition unit and a calculation and control unit.

The electrode array has a plurality of electrodes, which are arranged spaced apart from one another on the circumference of the body in the area of the thorax of a living being (the patient). The electrode array is arranged horizontally on or around the thorax of the patient. At least two of the electrodes of the electrode array are configured to feed an alternating current or an alternating voltage, and at least two of the remaining electrodes of the electrode array are configured to acquire measured signals.

The signal feed unit is configured and intended to feed an electrical feed signal to two feeding electrodes each varying cyclically and in a measuring cycle in each measuring run of a measuring cycle. An alternating current is preferably fed to the feeding electrodes.

The signal acquisition unit is configured and intended to acquire a plurality of measured signals from the plurality of electrodes in each of the measuring runs of the measuring cycle and to provide same to the calculation and control unit, as well as to a memory unit as EIT measuring channels for a further processing. In case of the preferred feeding of the alternating current to the feeding electrodes, voltage signals are obtained as measured signals to pairs of electrodes at the plurality of electrodes.

The calculation and control unit is configured and intended to carry out the processing of the acquired plurality of measured signals from the plurality of electrodes in each of the measuring runs of the measuring cycle. The calculation and control unit is further configured and intended to select the selected measured signals as selected EIT measuring channels from the acquired plurality of measured signals (EIT measuring channels) and to carry out a processing of the selected measured signals. The memory unit, which is configured and intended to store EIT measuring channels, measured signals, measured signals selected from the measured signals and signal traces and comparison data, such as comparison curve traces, pattern signal traces, and comparison threshold values and to provide for a further processing, addressing, preferably organized in vectors, data fields (matrices), is associated with the calculation and control unit.

The calculation and control unit is further configured to coordinate the memory unit, the signal feed unit and the signal acquisition unit. This coordination occurs such that the pair of signal-acquiring electrodes is rotated by the calculation and control unit over the plurality n of electrodes ($E_1 \ldots E_n$) within each measuring run and the pair of signal-feeding electrodes is rotated around the thorax in each measuring cycle, so that a number of n−3 measured signals is obtained in case of a number of n electrodes in a measuring run partial frame for each feed pair (pair of feeding electrodes) and a total number of n* (n−3) measured signals is obtained in a measuring cycle (time frame). The calculation and control unit is preferably configured, for example, as a central computer (CPU, µP) or arrangement of individual or a plurality of microcontrollers (µC).

The calculation and control unit is configured according to the present invention to determine a current elliptical circumferential shape of the electrode array on the thorax by means of selected measured signals, which are obtained from a selection of electrodes located opposite the two feeding electrodes and to determine and provide a control signal, which indicates the elliptical circumferential shape of the electrode array.

These measured signals, which are each obtained from the electrodes located opposite each of the two feeding electrodes, thus represent so-called opposite EIT measuring channels, on which the determination of the current elliptical circumferential shape of the electrode array on the thorax is based.

The elliptical circumferential shape of the electrode array on the thorax is determined by measured signals acquired at electrode pairs arranged opposite the two feeding electrodes on the thorax being selected from the measured signals of each measuring run of a measuring cycle and being stored as selected measured signals ($U_X$) by the calculation and control unit in interaction with the memory unit, mean values ($\overline{U}$) of the respectively selected measured signals of each electrode pair, arranged opposite the two feeding electrodes on the thorax being determined in each measuring run, and stored by the calculation and control unit in interaction with the memory unit in each measuring cycle, ratios (W) each from the selected measured signals ($U_X$) and the mean values ($\overline{U}$) determined for these selected electrodes being determined as a current signal trace (W1 . . . W16) of the selected electrodes by the calculation and control unit in interaction with the memory unit for each pair of electrodes of the selected electrodes, a comparison of the currently determined signal trace (W1 . . . W16) with at least one pattern signal trace (W_0) from a quantity of pattern signal traces being carried out by the calculation and control unit in interaction with the memory unit, wherein the pattern signal traces represent typical signal traces for various elliptical circumferential shapes of the electrode array on the thorax, the current elliptical circumferential shape of the electrode array on the thorax being determined by the calculation and control unit on the basis of the comparison, and a control signal, which indicates the currently determined elliptical circumferential shape of the electrode array, being generated and provided by the calculation and control unit.

The determination of the mean values ($\overline{U}$) on the basis of the number of selected measured signals $U_X$ of the electrodes located opposite the feeding electrodes in a measuring run can take place as arithmetic, geometric or quadratic averaging, as well as take place as a nonlinear averaging, for example, as a median filtering in the form of a "1 out of 3 filter" or "1 out of 5 filter."

The at least one pattern signal trace (W_0), as well as the quantity of pattern signal traces, which represent various typical elliptical circumferential shapes of the electrode array on the thorax, may be obtained both on the basis of measuring tests on test subjects with different circumferences of the thorax in the elliptical shape, as well as on the basis of theoretical considerations and/or simulated calculations on the spread of fed signals in case of different elliptical thorax shapes on the basis of the above-explained connections with arrangement and distribution of skeleton, organs and tissues in the thoracic space.

In a preferred embodiment of the electrical impedance tomography device, the calculation and control unit is configured to coordinate with an output unit which is arranged in or at the electrical impedance tomography device or is associated with the electrical impedance tomography device in addition to coordinating the signal feed unit, the signal acquisition unit, the memory unit.

This output unit is configured and intended for a graphic, pictorial, visual or numerical output of the data and/or information from the calculation and control unit, such as from impedances, impedance changes or impedance distributions in the area of the thorax determined from the acquired measured signals by the calculation and control unit by means of the control signal provided generated by the calculation and control unit. The output unit may be configured, for example, as a display device (display screen, monitor) or also as a graphics interface (HDMI, VGA, PAL), and may be configured by other types of monitors (smart phones, tablet PCs, laptop PCs) locally (LON, LAN, WLAN, field bus, Profi-BUS, CAN, POWERLINK) or remotely (Profi-NET, LAN), directly (USB, RS232) or indirectly (network, ETHERNET, Intranet, Internet), wireless (WLAN, Bluetooth) or wired (LAN).

In a preferred embodiment of the electrical impedance tomography device, two directly adjacent electrodes located opposite the two feeding electrodes are selected by the calculation and control unit in interaction with the signal feed unit as a respective pair of electrodes for acquiring the selected measured signals in each measuring run of the measuring cycle. Such a manner of carrying out electrical impedance tomography is designated as a so-called "adjacent data acquisition mode." In this connection, an overall image of the impedance distribution on the entire thorax is obtained on a regular basis, since measured signals of all electrodes one after the other in the measuring run of all measuring cycles contribute to the corresponding portion of information about the overall image. A jumping with a jumping over or skipping of individual electrodes in the signal feed or in the signal acquisition takes place in the so-called "adjacent data acquisition mode" only in situations, in which individual electrodes are identified as faulty (fault electrode). Furthermore, the variation of the signal feed takes place in such a so-called "adjacent data acquisition mode" such that in a measuring cycle, each of the two feeding electrodes is involved in the feed in the measuring cycle twice at most and each of the selected electrodes in a measuring run is taken into account in the acquisition of the selected measured signals twice at most.

In a preferred embodiment of the electrical impedance tomography device, the calculation and control unit applies a scaling in the determination of the ratio (W) from the selected measured signals ($U_X$) and from the mean values ($\overline{U}$) determined for these selected electrodes. The scaling applied brings about an amplification or highlighting of a signal difference between the selected measured signals and the mean values determined.

One practical possibility in the processing of the measured signals by the calculation and control unit in order to highlight or amplify the signal difference by means of scaling in the determination of the ratio (W), i.e., of the quotient of the selected measured signals and the mean values determined for these selected electrodes, is the incorporation of a mathematical function to the ratio (W), for example, of the logarithm (lg, ln, $\log_2$).

In a preferred embodiment of the electrical impedance tomography device, the calculation and control unit applies a logarithmic scaling in the determination of the ratio (W), preferably in a manner amplifying a signal difference, preferably in logarithmic scaling on the basis of 10

$$W = lg\left(\frac{U_{56X}}{\overline{U}_{56}}\right),$$

in logarithmic scaling on the basis of e $$W = \ln\left(\frac{U_{56X}}{\overline{U}_{56}}\right),$$

or
in logarithmic scaling on the basis of 2

$$W = \log_2\left(\frac{U_{56X}}{\overline{U}_{56}}\right).$$

In this manner, a concise shape of the signal trace is highlighted in the signal traces (W1 ... W16), and, as a result, concise shapes of the signal traces (W1 ... W16) of the ratio (W) corresponding to the plurality of electrodes are obtained. A so-called "W shape" is obtained, which illustrates the difference in the spread of the fed signals at the thorax to that effect, at which location of the elliptical circumferential shape (longer half-axis/shorter half-axis of the ellipse) the signal feed has taken place either at the shorter half-axis of the elliptical circumferential shape on the thorax, i.e., the so-called frontal axis (sternum-spine) of the plane of the array of the plurality of electrodes or at the longer half-axis of the elliptical circumferential shape on the thorax, i.e., the so-called transverse axis (left side of the body, right side of the body) of the plane of the array of plurality of electrodes.

In a preferred embodiment of the electrical impedance tomography device, a number of 3, 4, 5 or more than 6 electrodes of the electrodes located opposite the two feeding electrodes is selected by the calculation and control unit as selected electrodes for acquisition of the selected measured signals. The number of the electrodes selected by the calculation and control unit and located opposite the feeding electrodes for acquisition of the selected measured signals is selected differently in case of a different number (8, 12, 16, 32, 64) of the plurality of electrodes arranged on the thorax. Thus, for example, a selection of 4, 5 or 6 opposite electrodes for an effective formation of the ratio (W) with highlighting of the concise "W shape" is advantageous in case of a number of 16 electrodes. For a number of 8 electrodes, a selection of 2 to 4, for example, 3 opposite electrodes may be advantageous for a formation of the ratio (W), a selection of more than 6, for example, 8 to 12 opposite electrodes may be advantageous for a formation of the ratio (W) for a number of 32 electrodes.

In a preferred embodiment of the electrical impedance tomography device, measured signals selected by the calculation and control unit are each determined from mean values of the selected measured signals of one or a plurality of measuring cycles. For example, with 5-electrodes selected as selected electrodes opposite the stimulation electrodes, for a whole measurement cycle (frame) each set of 5 opposite electrode-pairs are selected and measured. These 5 electrodes are averaged for the selected measured signals ($U_x$). For example, if the pair (E1-E2) is the feed pair (is stimulated), the electrode pairs (E7-E8), (E8-E9), (E9-E10), (E10-E11), (E11-E12) are opposite of the stimulating pair (E1-E2) and an average value is calculated from the voltages of (E7-E8), (E8-E9), (E9-E10), (E10-E11), (E11-E12). The "x" in selected measured signals ($U_x$) further indicates that within the measurement cycle (frame) successively different pairs of electrodes are the selected electrodes used. As subsequent pairs of electrodes are the feed pairs of electrodes, for example by stimulating the pair (E2-E3), other opposite electrode pairs (E8-E9), (E9-E10), (E10-E11), (E11-E12), (E12-E13) are selected. In this case, the average of voltage ($U_x$) is calculated from the voltages of (E8-E9), (E9-E10), (E10-E11), (E11-E12), (E12-E13). Averaging the selected measured signals ($U_x$) of each selected electrode-pair provides 16 averaged voltages ($U_x$) out of one measurement cycle (frame) related to every stimulating electrode. The "x" additionally indicates, that the number of selected opposite electrode pairs could be other than 5 used and selected for averaging. Where for example only 2-electrodes have been selected, as the electrodes located opposite the feeding electrodes in a measuring run, there is no need for averaging or the averaging could be over several cycles. However, the averaging has advantages in regard to an electrode with bad skin contact. The incorporation of a plurality of measuring cycles for averaging is advantageous in terms of reducing the effects of disturbances that are superimposed by the measured signals. As a result, it is possible, for example, to achieve that the determined concise "W shape" of the signal traces (W1 . . . W16) is pronounced and largely free from distortions of the "W shape" and thus the comparison with the comparison (pattern) signal trace (W_0) with great unambiguity of the comparison result is possible. In this case, the averaging of the selected measured signals ($U_x$) of the electrodes located opposite the feeding electrodes over a plurality of measuring cycles may take place as arithmetic, geometric or quadratic averaging, as well as take place as a nonlinear averaging, for example, as a median filtering in the form of a "1 out of 3 filter" or "1 out of 5 filter." Averaging the signals ($U_x$) of each selected electrode-pair provides the averaged 16 voltages ($U_x$) out of one measurement cycle (frame) related to every stimulating electrode. A mean value ($\overline{U}$) is determined of all 16 average voltage ($U_x$) out of the 16 partial frames within one measurement cycle (frame).

In a preferred embodiment of the electrical impedance tomography device, the calculation and control unit is configured to calculate impedance values and/or impedance changes or impedance distributions in the thorax in the plane of the electrodes on the thorax on the basis of the plurality of measured values provided by the signal acquisition unit by means of an image reconstruction algorithm and to determine a tidal image on the basis of the calculated impedance values and/or impedance changes and/or impedance distributions in the thorax in the plane of the electrodes on the thorax and on the basis of the currently determined elliptical circumferential shape of the electrode array and to incorporate same into the control signal and to provide the control signal for the output unit. This makes it possible to take into account the currently determined elliptical circumferential shape of the electrode array in the tidal image by applying scaling operations to indexed vectors or indexed matrices with impedance values in the image reconstruction from the EIT measuring channels. In this connection, the currently determined elliptical circumferential shape of the electrode array on the thorax of an individual particular patient can be directly taken into account in case of correction for the tidal image, on the one hand, but, on the other hand, as an alternative and/or in addition, a deviation of the currently determined or actual individual elliptical circumferential shape of the electrode array on the thorax of the individual particular patient from a typical elliptical circumferential shape may also be determined. Thus, tidal images corrected and improved by the determined elliptical circumferential shape of the electrode array are obtained with the application of electrical impedance tomography, which are based in almost every application on a real arrangement and shape of an elliptical circumferential shape of the electrode array on the thorax without the user of the electrical impedance tomography device having to provide additional information, such as, for instance, circumference of the thorax, height, weight, gender or additional individual data of the patient to be examined, from which the circumferential shape of the patient can be determined approximately.

In another preferred embodiment, the output unit is configured to output and/or provide the currently determined elliptical circumferential shape on the basis of the control signal provided. The output and/or the provision preferably take place in a numerical manner, for example, as a scalar value, which represents an eccentricity of the elliptical circumferential shape of the electrode array or of the circumferential shape of the thorax or as a pair of values with corresponding values of dimensions of the shorter and longer half-axis of the currently determined elliptical circumferential shape.

The calculation and control unit may be configured as a central unit in the electrical impedance tomography device, which coordinates both the acquisition and analysis of the measured signals and initiates the determination and the provision of the control signal as well as the consideration of the control signal during the output of the corrected tidal image. A configuration of the calculation and control unit, in which a plurality of distributed units for acquisition, analysis and determination and provision of the control signal interact, for example, in the manner of the so-called cloud computer, instead of a central unit, may also be advantageous, however. A possible advantage from this may be achieved such that the correction of the tidal image and the provision thereof may take place at a location different from the location, at which measured signals are acquired.

All of the advantages that can be achieved with the described device can be achieved in an identical or similar manner with the method for the operation of an electrical impedance tomography device described as another aspect of the present invention.

A determination of an elliptical circumferential shape of an electrode array arranged on the thorax of a patient is carried out with a plurality of electrodes in a method according to the present invention for the operation of an electrical impedance tomography device according to the other aspect of the present invention.

This method for the operation of the electrical impedance tomography device is divided into a sequence of steps with the following steps:

An electrical feed signal is fed to two feeding electrodes each varying cyclically and in a measuring cycle in each measuring run of a measuring cycle in a first step.

Measured signals ($U_{56X}$), which are each selected at selected electrodes located opposite each of the feeding electrodes on the thorax, are acquired in each measuring run of a measuring cycle in a second step.

Mean values ($\overline{U}_{56}$) of each selected measured signal of each electrode pair of the respectively selected electrodes, which are arranged opposite each of the two feeding electrodes on the thorax, are determined in each measuring cycle in a third step.

A ratio, as a logarithmic ratio, is determined from the selected measured signals ($U_{56X}$) and the mean value ($\overline{U}_{56}$) determined for each of these selected electrodes to provide a plurality of ratios as a current signal trace (W1 ... W16) in a fourth step.

A comparison of the determined current signal trace (W1 ... W16) with at least one pattern signal trace (W_0) from a quantity of pattern signal traces is carried out, wherein the pattern signal traces represent different signal traces for different typical elliptical circumferential shapes of the electrode array on the thorax and a current elliptical circumferential shape is determined on the basis of the comparison, in a fifth step.

A control signal is generated and provided, which indicates the determined current elliptical circumferential shape of the electrode array on the thorax, in a sixth step.

The described embodiments represent each by themselves as well as combined with one another special configurations of the device according to the present invention and of the method according to the present invention for the operation of the electrical impedance tomography device with the electrode array with a plurality of electrodes arranged on the thorax of a patient. The advantages that are obtained due to a combination or combinations of a plurality of embodiments and additional embodiments are here nevertheless also covered by the inventive idea, even if not all combination possibilities of embodiments are each explained in detail for this.

The above-described embodiments of the method according to the present invention may also be configured in the form of a computer-implemented method as a computer program product with a computer, wherein the computer is prompted to carry out the above-described method according to the present invention, when the computer program is executed on the computer or on a processor of the computer or on a so-called "embedded system" as part of a medical device, especially of the EIT device. In this connection, the computer program may also be stored on a machine-readable storage medium. In an alternative configuration, a storage medium may be provided, which is intended for storage of the above-described, computer-implemented method and is readable by a computer.

It is within the framework of the present invention that not all steps of the method absolutely have to be executed on one and the same computer, but rather they may also be executed on different computers, for example, in a form and with media of so-called cloud computing in a data network system.

The sequence of the method steps may also optionally be varied. Furthermore, it is possible that individual sections of the above-described method can be executed in a separate unit, for example, which can be sold separately (e.g., on a data analysis system preferably arranged in the vicinity of the patient), other parts on a different unit which can be sold (e.g., on a display and visualization unit, which is, for example, preferably arranged in a plurality of patient rooms for monitoring as a part of a hospital information system), as a distributed system so to speak.

The advantages described for the method according to the present invention can be achieved in an identical or similar manner with the device according to the present invention as well as with the described embodiments of the device. Furthermore, the described embodiments and their features and advantages of the method can be extrapolated to the device, and the described embodiments of the device can be extrapolated to the method.

The corresponding functional features of the method are configured here by corresponding concrete modules of a device, and in particular by hardware components (CPU, µC, DSP, MP, FPGA, ASIC, GAL), which can be implemented, for example, in the form of a processor, a plurality of processors (µC, µP, DSP) or in the form of instructions in a memory area that are processed by the processor.

The present invention shall now be explained in detail by means of the following figures and the corresponding figure descriptions without limitations of the general inventive features. The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
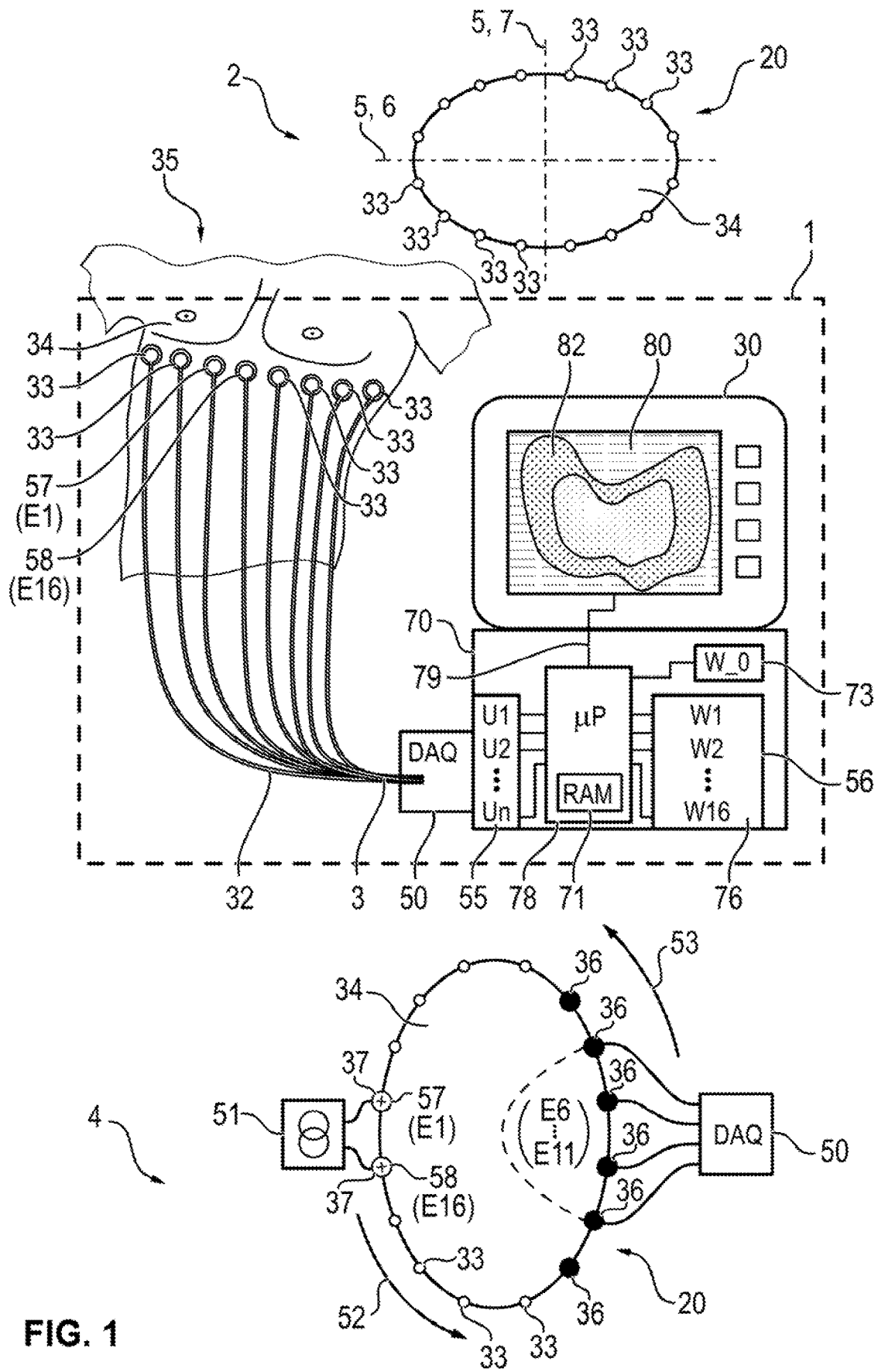
FIG. 1 is a schematic view of functional components of an electrical impedance tomography device.

Referring to the drawings, FIG. 1 shows an impedance tomography device 1. A number of electrodes 33 is arranged on the thorax 34 of a patient 35 in the impedance tomography device. EIT data 3 are transmitted from the electrodes 33 to a calculation and control unit 70 by means of a data acquisition unit 50. The EIT data 3 are transmitted from the electrodes 33 by means of wired connections 32. A processor unit 78 and a memory 71 are arranged in the calculation and control unit 70. The processor unit 78 processes the EIT data 3, which are provided by the signal acquisition unit 50. It is shown in this FIG. 1 that the EIT data 3 reach the calculation and control unit 70 with the processor unit 78 as measured signals 55. The processor unit 78 determines measured signals ($U_{56X}$) 56 selected from the measured signals 55 by means of suitable calculation methods and algorithms the processor unit 78 determines and a current signal trace (W1 ... W16) 76. Selected measured signals 56 are in this connection those measured signals that are obtained from selected electrodes 36 located opposite the signal-feeding electrodes 37. This can be seen in detail in a schematic feed and acquisition view 4 of the signal feed and the signal acquisition. At least one pattern signal trace (W_0) 73 is used in the calculation and control unit 70 to analyze selected measured signals ($U_{56X}$) 56 or a current signal trace 76 (W1 . . . W16) determined from the measured signals ($U_{56X}$) 56 (FIG. 3, FIG. 4) by means of a comparison. As a result of the analysis of the comparison, a control signal 79, which indicates a current elliptical circumferential shape 20' (FIG. 4) of the electrodes 33 combined into an electrode array, is obtained. The control signal 79 is made available to an EIT device 30 with an output unit 80 as shown in FIG. 1. The output unit 80 makes possible a visualization 82 of the impedances and of the impedance changes determined from the measured signals 55 by the calculation and control unit 70. The visualization 82 is in the horizontal plane of the thorax 34 in a so-called dorsal view.

An electrode view 2 of an array of electrodes 33 on the thorax 34 above the impedance tomography device 1 is schematically shown in FIG. 1. A space coordinate system 5 with an X axis 6 and a Y axis 7 is shown. The electrodes 33 are arranged approximately uniformly distributed about the thorax 34. This electrode view 2 represents a horizontal section through the thorax 34 in the plane of the array of electrodes 33, i.e., the visualization plane of the dorsal view for the visualization at 82 so to speak. The schematic electrode view 2 shows a typical elliptical circumferential shape 20, which is typical for the majority of human beings in the area of the array of electrodes 33 around the thorax 34. The schematic electrode view 2 of electrodes 33 on the thorax 34 has a number of 16 electrodes. In the schematic view 4 of the signal feed and the signal acquisition, a current is fed to two electrodes, namely to the electrode E1 57 and to the electrode E16 58 by means of a signal feed unit 51. Located opposite the two feeding electrodes E1 57, E16 58, selected measured signals 56 are acquired by means of the signal acquisition unit 50 as a current signal trace 76, in a run of a signal acquisition, at a selection of at least two electrodes 36.

Figure 3:
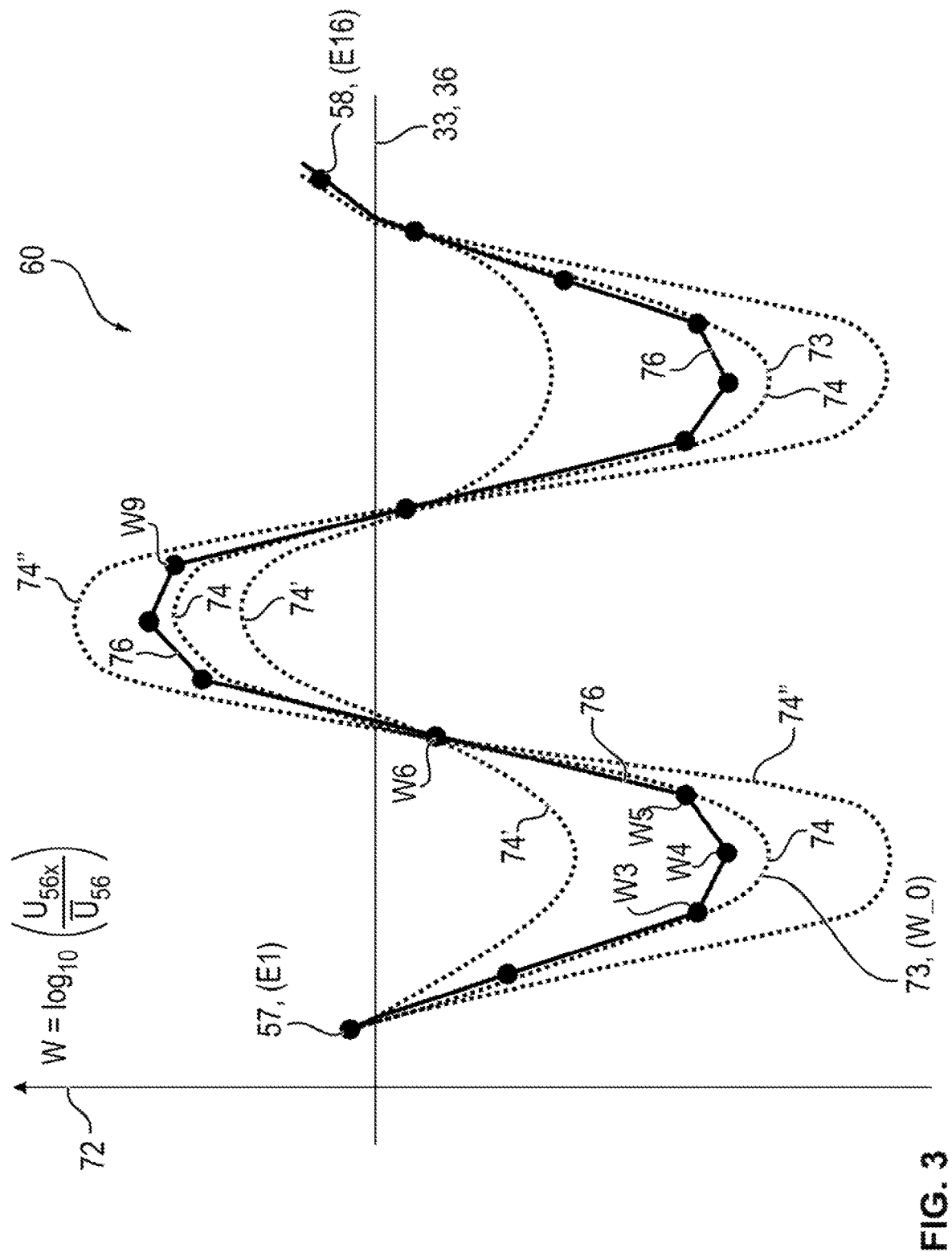
FIG. 3 is signal traces in case of different elliptical circumferential shapes of electrode arrays.
Figure 4:
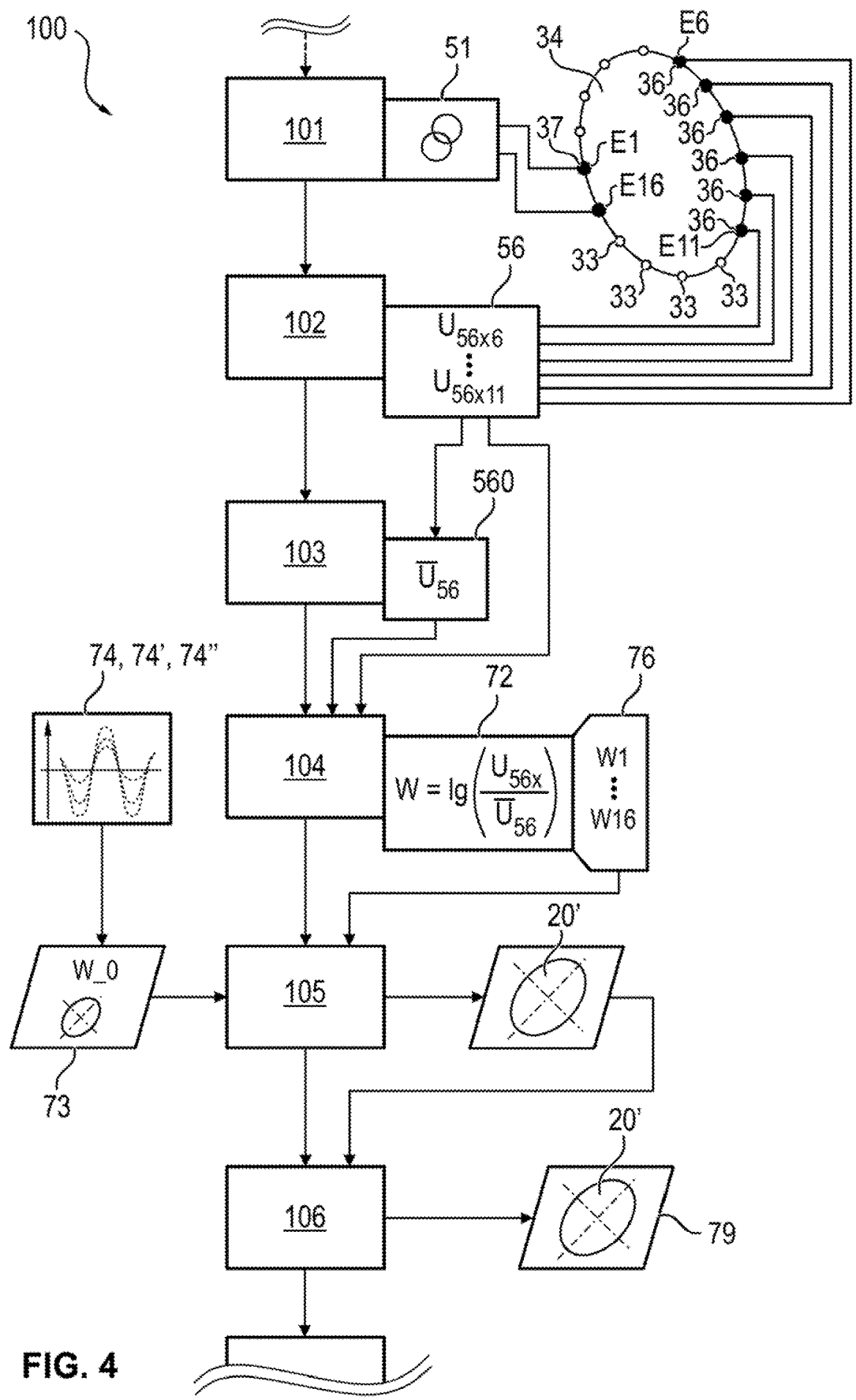
FIG. 4 is a flow chart for a determination of an elliptical circumferential shape of an electrode array on the thorax.

FIG. 1 shows the at least two electrodes E6-E11, for example, as a selection of 6 electrodes 36. However, in the sense of the present invention, it is also covered that a number different than the shown 6 selected electrodes 36, for example, 5, 4, 3 electrodes, which are arranged opposite the feeding electrodes 37, may also be used for analysis for determination of elliptical circumferential shapes 20, 21, 22 (FIG. 2) of the thorax 34 of the patient 35. After the feed to the electrodes E1, E16, 57, 58 by the signal feed unit 51, the feed to the next pair of feeding electrodes, i.e., the electrodes E16 and E15, is carried out, in this FIG. 1, shown as a counterclockwise rotation 52. The signal acquisition is then likewise carried out by means of a counterclockwise rotation 53 as shown in this FIG. 1 at the selected electrodes E5-E10 located opposite the electrodes E15 and E16. The rotations 52, 53 of feed and signal acquisition are carried out in a measuring cycle for all pairs of adjacent electrodes of the 16 electrodes E1-E16. A quantity of selected measured signals ($U_{56X}$) 56 is obtained in this manner. Thus, a measured signal ($U_{56X}$) 56 is assigned to each pair of acquiring electrodes 36. These selected measured signals ($U_{56X}$) 56 obtained in the measuring cycle, each obtained by pairs of electrodes 36 each pair of electrodes 36 located opposite the feeding electrodes 37 for a measuring run, are further processed by the calculation and control unit 70 as a current signal trace (W1 . . . W16) 76 and compared as such with at least one pattern signal trace (W_0) 73 from a quantity of pattern signal traces 74, 74', 74" (FIG. 3). The pattern signal traces 74, 74', 74" (FIG. 3) represent in this case signal traces for different typical elliptical circumferential shapes of the electrode array 33 on the thorax 34. The control signal 79 is determined from the result of the comparison. The details on a generation of the control signal 79 and the further processing and analysis or use of the control signal 79 appear from the views in FIGS. 2, 3 4 and the corresponding descriptions. A current elliptical circumferential shape 20' (FIG. 4) is determined here as a result; as an alternative and/or in addition, a deviation of the currently determined or actual individual elliptical circumferential shape 21, 22 (FIG. 2) of the thorax 34 of an individual patient 35 from a typical elliptical circumferential shape 20 may also be determined. This result, i.e., the determined current circumferential shape 20' (FIG. 4), or the determined deviation from the typical circumferential shape 20 is utilized by means of the control signal 79 to adapt the visualization 82 in the output unit 80 by means of a correction to the currently determined or actual individual elliptical circumferential shape 20' (FIG. 4). This makes it possible that a high-quality electrical impedance tomography measurement can be carried out with the EIT device 30 even for elliptical circumferential shapes deviating from typical circumferential shapes. Thus, a possibility to calibrate the actual individual elliptical circumferential shape on the thorax 34 of a patient 35 to be examined is provided before carrying out additional examinations or measurements with the EIT device 30, so to speak.

Figure 2:
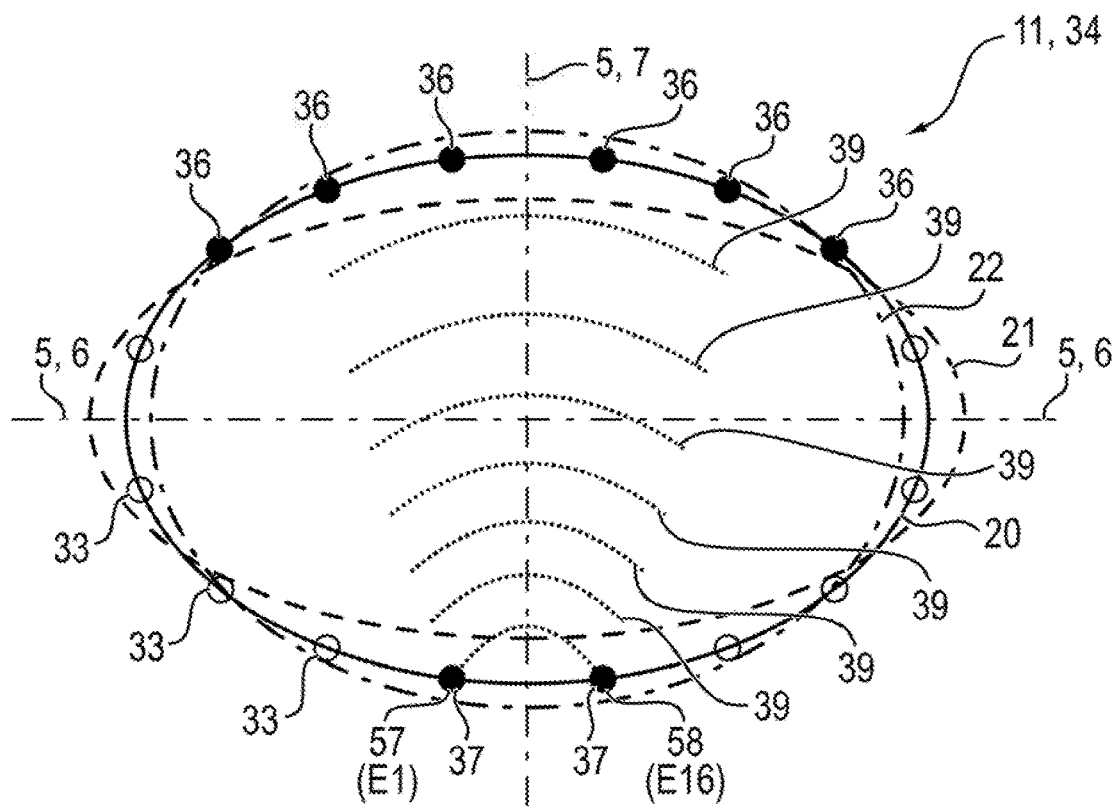
FIG. 2 is two views of different constellations of electrode arrays positioned at different elliptical circumferential shapes.
Figure 2:
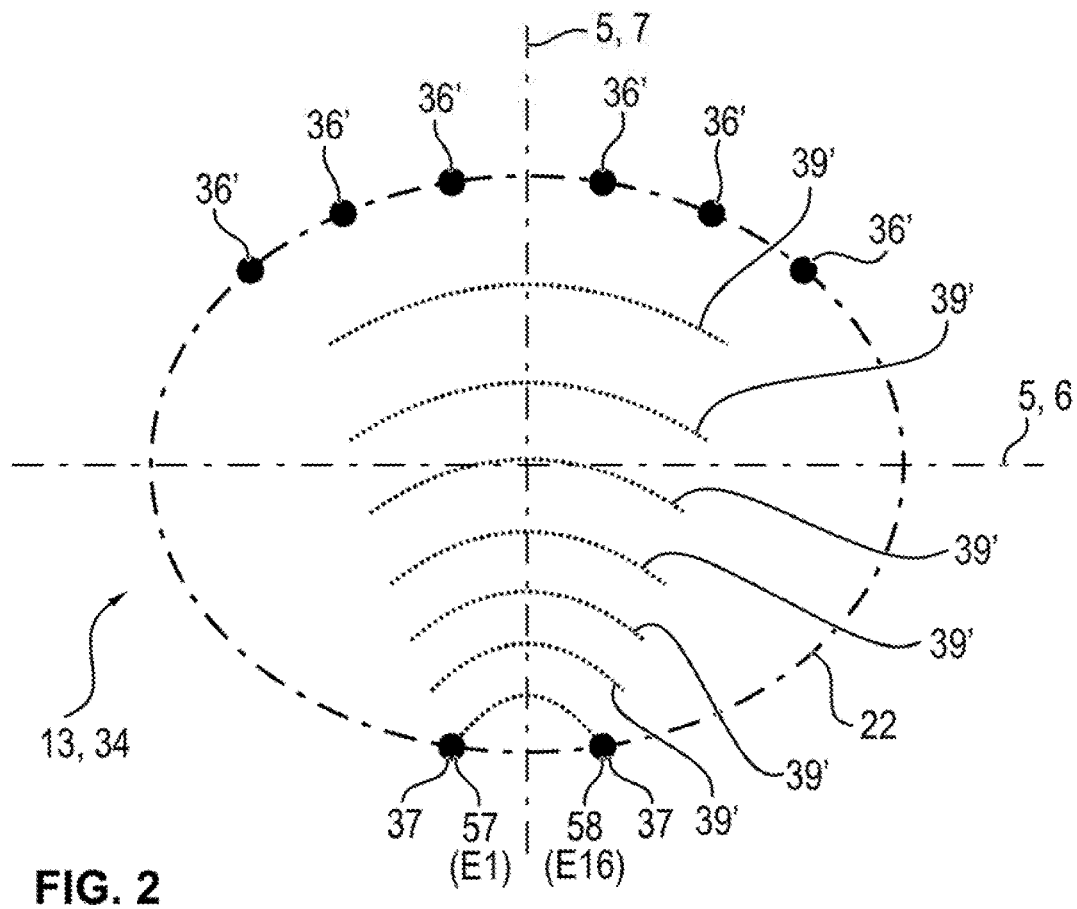

An electrode array comprising a plurality of electrodes 33 at a first elliptical circumferential shape 11 and an electrode array at a second elliptical circumferential shape 13 of a thorax 34 of a patient 35 (FIG. 1) is shown in FIG. 2. Identical components in FIGS. 1 and 2 are designated by identical reference numbers in FIGS. 1 and 2. A space coordinate system 5 with an X axis 6 and a Y axis 7 is plotted in each of the two elliptical circumferential shapes 11, 13 of the thorax 34. The view of the first elliptical circumferential shape 11 shows an elliptical circumferential shape 20 (plotted as a solid line) and two other elliptical circumferential shapes 21, 22 (shown as a dashed or a dotted-dashed line). The two other elliptical circumferential shapes 21, 22 have a difference to the elliptical circumferential shape 20 to the effect that these three circumferential shapes 20, 21, 22 are elliptically different from one another. These three different elliptical circumferential shapes 20, 21, 22 have each different expansions in the two horizontal axes (front side of the body/rear side of the body, left/right side of the body). The elliptical circumferential shape 20 in this FIG. 1 may be, for example, consistent with a typical elliptical circumferential shape.

In the electrode array of the first elliptical circumferential shape 11, as described concerning FIG. 1, an electric current is fed to the electrodes E1 57 and E16 58 as feeding electrodes 37. The signals fed by the feeding electrodes 37 reach the opposite electrodes 36 (E6 . . . E11) as a spread of the feed 39 in the thorax 34. The opposite electrodes 36 are the electrodes E6-E11 in this FIG. 2. In the electrode array at the second elliptical circumferential shape 13, the elliptical circumferential shape 22 is plotted in the electrode array of the first elliptical circumferential shape, which is again shown in detail with an arrangement of the feeding electrodes 37 and opposite signal-acquiring electrodes 36' (E6 . . . E11). A spreading 39' of the feed signals in and through the thorax 34 to the opposite electrodes 36' is obtained, which is different compared to the electrode array at the first elliptical circumferential shape 11. A number of 6 electrodes is selected as a selection of electrodes 36, 36' from electrodes 33 that are arranged opposite the feeding electrodes 37, in this FIG. 2. It is also, however, covered in the sense of the present invention that other numbers of selected electrodes, for example, 3, 4, 5 or more than 6 electrodes may also function as selected electrodes 36, 36'. The differences in the spreads 39, 39' have an effect on the pattern signal traces 74, 74', 74" (FIG. 3) and/or on the current signal trace 76 (FIG. 3), as will be explained and described in detail in the description on FIG. 3.

FIG. 3 shows in a signal view 60—for reasons of graphic simplification—three different pattern signal traces 74, 74', 74", which are characteristic for three typical elliptical circumferential shapes of electrode arrays on the thorax 34 (FIG. 2). The pattern signal traces 74, 74', 74" are shown in dotted line in this FIG. 3. Furthermore, a current signal trace (W1, W2 . . . W16) 76 based on selected measured values ($U_{56X}$) 56 is shown, wherein the measured values ($U_{56X}$) 56 are related to the electrodes 33 E1 57 and E16 58. The measured values 56 are connected to one another in the view of FIG. 3 by means of a solid line. The current signal trace 76 is also analyzed in a process 100 shown in FIG. 4.

The pattern signal traces 74, 74', 74" and the current signal trace 76 represent in this example signal ratios (W) 72 of a weighted logarithmic ratio $$W = \log 10\left(\frac{U_{56X}}{\overline{U}_{56}}\right)$$

of the individual measured signals ($U_{56X}$) 56 from the selected electrodes 36 to mean value ($\overline{U}_{56}$) of the measured signals of the selected electrodes 36. The current signal trace (W1, W2 . . . W16) 76 is shown on the basis of selected measured voltages 56 of the selected electrodes 36 (FIG. 1) each located opposite the feed 37 (FIG. 1). The current signal trace (W1, W2 . . . W16) 76, as well as the pattern signal traces 74, 74', 74", have a "w-shaped" trace, figuratively speaking A pronouncement of this "W shape" of varying significance is obtained depending on the elliptical shape of the electrode array on the circumference of the thorax and thus also depending on the elliptical shape of the circumference of the thorax itself. The described "W shape" is all the more pronounced with its minima and maxima, the greater is the expansion of the ellipse in the direction of the horizontal axis 6 (FIG. 1) in the space coordinate system 5 (FIG. 1). In FIG. 3, the signal trace 74 is that pattern signal trace which has the greatest possible consistency of the pattern signal traces 74, 74', 74" with the current signal trace 76. Therefore, this pattern signal trace 74 is obtained in this FIG. 3, for example, as the at least one pattern signal trace (W_0) 73, as it is also used in FIG. 1 and FIG. 4. The typical elliptical circumferential shape stored under this at least one pattern signal trace (W_0) 73 describes in this case a corresponding typical ratio of the lengths of the shorter half-axis 7 (FIG. 1) to the longer half-axis 6 (FIG. 1) for a circumferential shape, which is, for example, approximately consistent with the circumferential shape 20 (FIGS. 1, 2) shown in FIG. 2. The result of this comparison is in this case further processed into a control signal 79 (FIG. 1) by the calculation and control unit 70 (FIG. 1).

The control signal 79 (FIG. 1) may in this case directly indicate a determined current circumferential shape 20', on the one hand (FIG. 4). The control signal 79 (FIG. 1) may, on the other hand, also indicate, with which at least one pattern signal trace (W_0) 73 from the quantity of pattern signal traces 74, 74', 74" the current signal trace 76 has the greatest possible consistency and additionally also still contain information in an advantageous configuration, depending on how well the consistency is between the current signal trace 76 and the at least one pattern signal trace (W_0) 73. In this example according to FIG. 3, the pattern signal trace 74 has the best possible consistency with the current signal trace 76. The determination of the greatest possible consistency may in this case be carried out by means of mathematical regression calculation (Fit, regression analysis), for example, by means of the "least mean squares method."

The control signal 79 (FIG. 1) can be used for further data processing of the EIT data 3 (FIG. 1) when applying the electrical impedance tomography by the EIT device, for example, 30 (FIG. 1) for the visualization 82 (FIG. 2) on the output unit 80 (FIG. 1). Such a use is, for example, the incorporation of the determined elliptical circumferential shape or the deviation from a predefined typical circumferential shape of the thorax 34 (FIG. 1, FIG. 2) in the image reconstruction algorithm to obtain the image data for the visualization 82 (FIG. 1) of the impedance distribution in the dorsal view (FIG. 1) on the basis of the measured signals 55 (FIG. 1).

FIG. 4 shows a process 100 for operating an electrical impedance tomography device 30 (FIG. 1) with a sequence of steps 101 through 106 for a determination of an elliptical circumferential shape (20') of an electrode with a plurality of electrodes 33 arranged on the thorax 34 of a patient 35 (FIG. 1). Identical components in FIGS. 1, 2, 3 and 4 are designated by identical reference numbers in FIGS. 1, 2, 3, 4.

The sequence of steps 101 through 106 begins from an ongoing measurement operation or after a start-up of the electrical impedance tomography device 30 (FIG. 1) such that an electrical feed signal is fed by means of a signal feed unit 51 to two feeding electrodes 37 each varying cyclically and in a measuring cycle in each measuring run of a measuring cycle in a first step.

Measured signals ($U_{56X}$) 56, which are each selected at selected electrodes 36 located opposite each of the feeding electrodes 37 on the thorax 34 are acquired in each measuring run of a measuring cycle in a second step 102.

Mean values ($\overline{U}_{56}$) 560 of each selected measured signal 56 of each electrode pair of the respectively selected electrodes 36, which are arranged opposite each of the two feeding electrodes 37 on the thorax 34, are determined in each measuring run in a third step 103.

A logarithmic ratio (W) 72, for example, $$W = lg\left(\frac{U_{56X}}{\overline{U}_{56}}\right),$$

$$W = \ln\left(\frac{U_{56X}}{\overline{U}_{56}}\right), \text{ or}$$

$$W = \log_2\left(\frac{U_{56X}}{\overline{U}_{56}}\right)$$

is determined from the selected measured signals ($U_{56X}$) 56 and the mean value ($\overline{U}_{56}$) 560 determined for these selected electrodes 36 as a current signal trace (W1, W2 . . . W16) 76 in a fourth step 104.

A comparison of the determined current signal trace 76 with at least one pattern signal trace (W_0) 73 is carried out in a fifth step 105. The at least one pattern signal trace (W_0) 73 represents in this FIG. 4 a pattern signal trace from a quantity of pattern signal traces (comparison signal traces) for typical elliptical circumferential shapes of the electrode array on the thorax 34 (FIG. 1). A current elliptical circumferential shape 20' of the electrode array on the thorax 34 (FIG. 1) is determined by means of this comparison.

A control signal 79 is generated and provided, which indicates the determined current elliptical circumferential shape 20' of the electrodes 33 (FIG. 1) on the thorax 34 (FIG. 1), in a sixth step 106.

Figure 5:
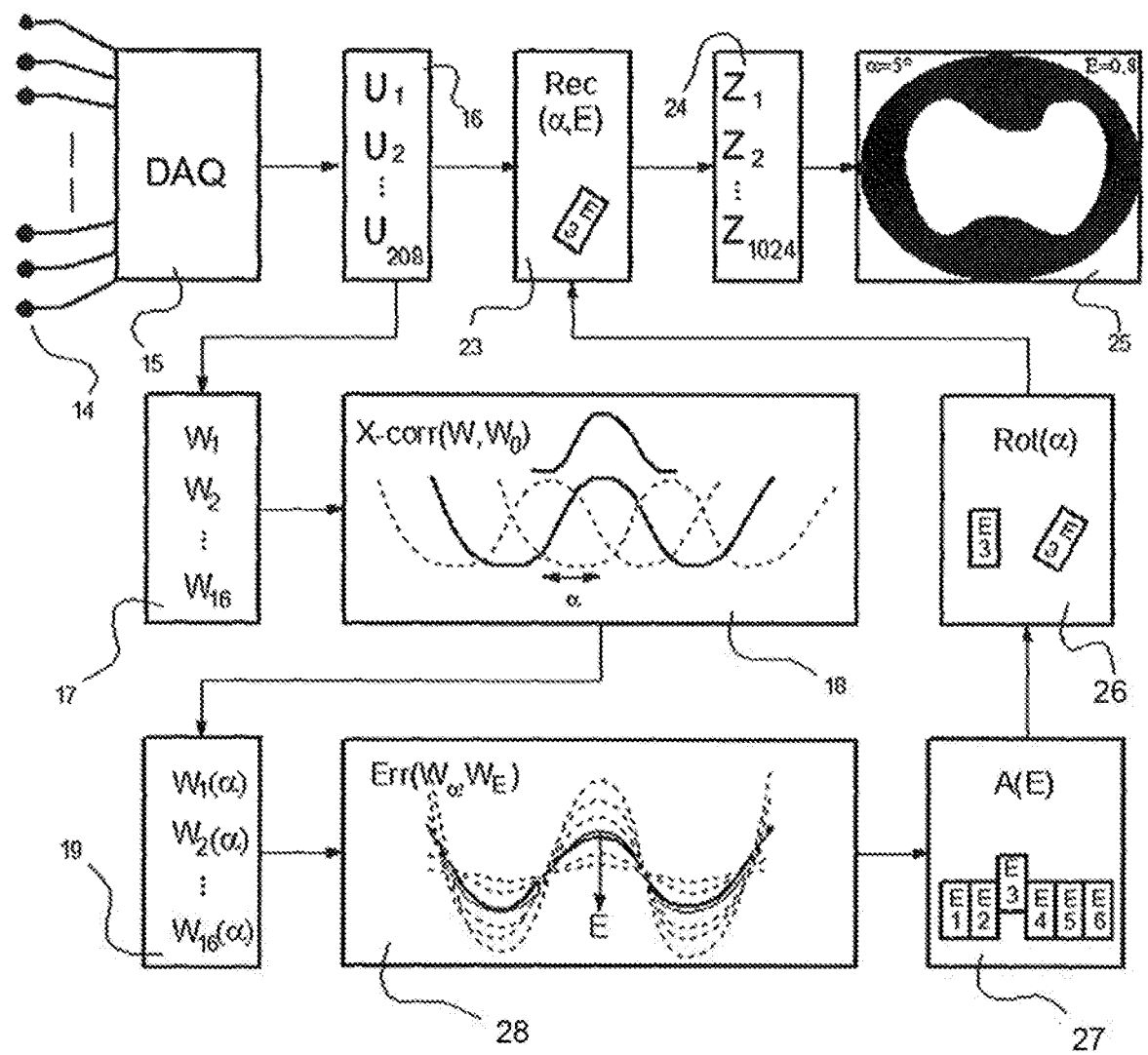
FIG. 5 is a schematic view of functional components related to the reconstruction matrix and display.

FIG. 5 shows aspects of the device and method with a display 25 of an optimal ellipsoidal match corrected EIT-image. The display 25 also provides a visualization 82 with a display of the axial twist and/or shape E relative to optimal ellipsoidal match. FIG. 5 shows the determined set 17 of signal trace 60 (W1 . . . W16) with the type of ellipsoidal shape determined at 28. FIG. 5 also shows the optional further calculation at 18 to determine an axial twist α of the electrode array and to provide a signal trace that is a function of the twist angle W1(α) . . . W16(α) at 19 (optional). The determination of the axial twist α of the electrode array is described in an application attached hereto as an appendix (and incorporated herein by reference in its entirety). With the elliptical shape determination A at 28 with elliptical shape comparison 27, the control signal 79 is generated based on the optimal ellipsoidal match A(E). A control signal for of the axis twist calculated at 18 (if any) may be generated at 26 of the optimal rotation vector Rot(α). The optimal ellipsoidal match A(E) is used to determine a final reconstruction matrix at 23 (Rec(α,E)). The impedance values Z1, Z2 . . . Z1024 are calculated at 24 based on final reconstruction matrix (Rec(α,E)). In a preferred embodiment of the electrical impedance tomography device, the calculation and control unit is configured to calculate impedance values and/or impedance changes or impedance distributions Z1, Z2 . . . Z1024 in the thorax in the plane of the electrodes on the thorax on the basis of electrode input 14 of the plurality of measured values (indicated at 16) provided by the signal acquisition unit 15 by means of an image reconstruction algorithm 23 and to determine a tidal image on the basis of the calculated impedance values and/or impedance changes and/or impedance distributions in the thorax in the plane of the electrodes on the thorax and on the basis of the currently determined elliptical circumferential shape of the electrode array and to incorporate same into the control signal and to provide the control signal for the output unit. This makes it possible to take into account the currently determined elliptical circumferential shape of the electrode array in the tidal image by applying scaling operations to indexed vectors or indexed matrices 23 with impedance values in the image reconstruction from the EIT measuring channels. The reconstruction matrix may be based on a known reconstruction algorithms such as disclosed in WO 2015/048917 and U.S. Pat. No. 6,236,886 (each reference is incorporated herein by reference in its entirety). The data processing represented at 23 in FIG. 5 comprises a reconstruction algorithm provided at the data processor in order to determine and to reconstruct the electrical properties from the measured values 55. In case of the reconstruction of the electrical properties from the acquired measured data, a shape model may be selected from a plurality of shape models on the basis of the type of ellipsoidal shape 28 (and/or axis twist calculated at 18). In the alternative the known reconstruction algorithm may be adapted with a regularization, similar to that provided for differences in densities, to address or eliminate the effect of different ellipsoidal shape form and/or to address any axial twist. At a time of initialization of the EIT-system, after attaching the electrodes and starting the EIT device, the actual ellipsoidal shape form and/or actual axial twist α in comparison to a default or standard ellipsoidal shape and/or default or standard axial twist α is determined. In this connection, the currently determined elliptical circumferential shape of the electrode array on the thorax of an individual particular patient can be directly taken into account in case of correction for the tidal image, on the one hand, but, on the other hand, as an alternative and/or in addition, a deviation of the currently determined or actual individual elliptical circumferential shape of the electrode array on the thorax of the individual particular patient from a typical elliptical circumferential shape may also be determined. Thus, tidal images corrected and improved by the determined elliptical circumferential shape of the electrode array are obtained with the application of electrical impedance tomography, which are based in almost every application on a real arrangement and shape of an elliptical circumferential shape of the electrode array on the thorax without the user of the electrical impedance tomography device having to provide additional information, such as, for instance, circumference of the thorax, height, weight, gender or additional individual data of the patient to be examined, from which the circumferential shape of the patient can be determined approximately.

While specific embodiments of the invention have been shown and described in detail to illustrate the application of the principles of the invention, it will be understood that the invention may be embodied otherwise without departing from such principles.

APPENDIX

List of Reference Designations

1 Electrical impedance tomography device
2 Schematic view of an array of electrodes on the thorax
3 EIT signals, EIT data
4 Schematic view of signal feed and signal acquisition
5 Space coordinate system
6 X axis
7 Y axis
11 Electrode array at a first elliptical circumferential shape
13 Electrode array at a second elliptical circumferential shape
14 electrode inputs
15 Data acquisition unit
16 set of measured signals
17 set of signal traces
18 axial twist determination (optional)
19 Axial twist values
20 Elliptical circumferential shape
21 Calculating/using an optimal ellipsoidal match A(E)
22 Determining/using the optimal rotation vector Rot(α)
23 Determining a final reconstruction matrix
24 Calculation of impedance values Z based on reconstruction matrix with Rec(α and/or E)
25 Calculating image with optional display of axial twist and/or shape relative to optimal ellipsoidal match
26 Axial twist comparison
27 Elliptical shape comparison
28 elliptical shape determination
20' Current elliptical circumferential shape of the thorax
20, 21, 22 Elliptical circumferential shapes of the thorax
30 EIT device
32 Wired connections, feed lines of the electrodes
33 Electrodes E1 . . . E16, electrode array
34 Thorax, circumference of thorax
35 Patient 36, 36' Selection of electrodes, located opposite feeding electrodes
37 Feeding electrodes
39, 39' Spread of the feed in the thorax
50 Signal acquisition unit (DAQ)
51 Signal feed unit
52 Run of the signal feeds (measuring cycle, frame)
53 Run of the signal acquisitions (measuring run, partial frame)
55 Measured signals U1 ... Un
56 Selected measured signals $U_{56X}$
57 Electrode E1
58 Electrode E16
60 Signal display
70 Calculation and control unit
71 Memory
72 Signal ratio, weighted amplitude ratio, ratio (W)
73 Pattern signal trace (W_0)
74, 74', 74" Pattern signal traces
76 Current signal trace (W1 ... W16)
78 Processor unit (µP, µC, CPU)
79 Control signal
80 Output unit, display screen
82 Visualization
100 Process
101-106 Sequence of steps
560 Mean values ($\overline{U}_{56}$)

What is claimed is:

1. A method for the operation of an electrical impedance tomography device for a determination of an elliptical circumferential shape of an electrode array comprising a plurality of electrodes arranged on a thorax of a patient, the method comprising:
    feeding an electrical feed signal to two feeding electrodes of the electrodes in each measuring run with the two feeding electrodes varying cyclically in a measuring cycle comprised of a plurality of measuring runs;
    selecting measured signals at selected electrodes located opposite each of the feeding electrodes and acquiring the selected measured signals in each measuring run of a measuring cycle;
    determining a mean value ($\overline{U}_{56}$) of each selected measured signal ($U_{56X}$) of each electrode pair of the respectively selected electrodes in each measuring run;
    determining a logarithmic ratio comprising $$W = lg\left(\frac{U_{56X}}{\overline{U}_{56}}\right),$$

$$W = \ln\left(\frac{U_{56X}}{\overline{U}_{56}}\right), \text{ or}$$

$$W = \log_2\left(\frac{U_{56X}}{\overline{U}_{56}}\right)$$

from each of the selected measured signals ($U_{56X}$) and the mean values ($\overline{U}_{56}$) for the selected electrodes, as a current signal trace;
    comparing the determined current signal trace with at least one pattern signal trace from a quantity of pattern signal traces, wherein the pattern signal traces represent different signal traces for different typical elliptical circumferential shapes of the electrode array on a thorax and a current elliptical circumferential shape is determined on the basis of the comparison; and
    generating a control signal which indicates the determined current elliptical circumferential shape of the electrode array on the thorax and providing the generated control signal as an output.

2. A method in accordance with claim 1, wherein a number of three or more electrodes of the electrodes which are located opposite the two feeding electrodes is selected as the selected electrodes for acquisition of the selected measured signals.

3. A method in accordance with claim 1, wherein the selected measured signals are each determined from mean values of the selected measuring pairs of electrodes of a plurality of measuring cycles.

4. A method in accordance with claim 1, further comprising providing the electrical impedance tomography device, wherein the electrical impedance tomography device comprises:
    the electrode array having the plurality of electrodes arranged spaced apart from one another on a circumference of a body of the patient in an area of the thorax of the patient;
    a calculation and control unit configured to process the measured signals of the plurality of electrodes and to select selected measured signals from the acquired plurality of measured signals and to process the selected measured signals; and
    a non-transitory memory unit, which non-transitory memory unit is associated with the calculation and control unit.

5. A method in accordance with claim 4, wherein:
    two directly adjacent electrodes which are located opposite the two feeding electrodes are each selected as a respective electrode pair for acquiring the selected measured signals; and
    the calculation and control unit in each measuring run of the measuring cycle carries out a variation of the two feeding electrodes such that in a measuring cycle, each of the two feeding electrodes is involved in a signal feed in the measuring cycle at most twice in one measuring cycle and each of the selected electrodes is taken into account twice at most during the acquisition of the selected measured signals in each measuring run.

6. A method in accordance with claim 4, wherein the electrical impedance tomography device further comprises an output unit wherein the calculation and control unit is configured to coordinate the output unit, wherein the output unit is arranged in or at the electrical impedance tomography device or is associated with the electrical impedance tomography device.

7. A method in accordance with claim 6, wherein an output unit is configured to provide the currently determined elliptical circumferential shape on the basis of the control signal provided.

8. A method in accordance with claim 4, wherein the calculation and control unit is configured:
    to calculate at least one of impedance values, impedance changes, and impedance distributions in the thorax in the plane of the electrodes on the thorax on the basis of the plurality of measured values by means of an algorithm for image reconstruction; and
    to determine at least one of a tidal image on the basis of the calculated impedance values, impedance changes, and impedance distributions in the thorax in the plane of the electrodes on the thorax and on the basis of the currently determined elliptical circumferential shape of the electrode array and to incorporate same into the control signal and to provide the control signal for the output unit.

* * * * *